United States Patent [19]

Bettle, III et al.

[11] 4,314,949

[45] Feb. 9, 1982

[54] PROCESS FOR MAKING PEROXYCARBOXYLIC ACIDS

[75] Inventors: Griscom Bettle, III, Cincinnati; Howard Mills, Forest Park; Edward B. Richter, Cincinnati, all of Ohio

[73] Assignee: The Procter & Gamble Company, Cincinnati, Ohio

[21] Appl. No.: 171,564

[22] Filed: Jul. 23, 1980

[51] Int. Cl.$^3$ .......................................... C07C 179/00
[52] U.S. Cl. ................................................ 260/502 R
[58] Field of Search ................................... 260/502 R

[56] References Cited

U.S. PATENT DOCUMENTS

| | | | |
|---|---|---|---|
| 2,813,896 | 11/1957 | Krimm | 260/502 R |
| 2,816,147 | 12/1957 | Weber et al. | 260/502 R |
| 3,140,312 | 7/1964 | Kurhajec et al. | 260/502 R |
| 3,655,738 | 4/1972 | Nielsen | 260/502 R |
| 3,819,688 | 6/1974 | Silbert et al. | 260/502 R |
| 4,085,133 | 4/1978 | Briody | 260/502 R |
| 4,087,455 | 5/1978 | Prescher et al. | 260/502 R |
| 4,088,676 | 5/1978 | Hofen et al. | 260/502 R |
| 4,119,660 | 10/1978 | Hutchins | 260/502 R |
| 4,147,720 | 4/1979 | Berkowitz | 260/502 R |
| 4,244,884 | 1/1981 | Hutchins | 260/502 R |

FOREIGN PATENT DOCUMENTS 744391 10/1966 Canada .

OTHER PUBLICATIONS

Parker et al., "J. American Chemical Society", vol. 77, pp. 4037-4041 (1955).
Swern, "Organic Peroxides", Wiley Interscience, (1970), vol. 1, pp. 315-318 and 344-345.

*Primary Examiner*—Werren B. Lone
*Attorney, Agent, or Firm*—R. B. Aylor; T. H. O'Flaherty; R. C. Witte

[57] ABSTRACT

An improved process, preferably continuous, for making a peroxyacid having about 6 to 18, preferably about 8 to 16 carbon atoms and at least one peroxyacid moiety, using as starting materials the corresponding carboxylic acid and hydrogen peroxide and using concentrated acid as the reaction medium, comprising the steps of (a) maintaining a reaction mixture having a liquid component comprising 60 to 80% concentrated acid, 2.5 to 12.5% hydrogen peroxide, and 7.5 to 37.5 % water and a dispersed solid component comprising crystals of the carboxylic acid starting material and peroxyacid product, the ratio of liquid to solids being from about 15:1 to about 49:1. Preferably the carboxylic acid is added as particles having a size of less than #100 mesh to a preformed solution of the concentrated acid and peroxide.

7 Claims, No Drawings

PROCESS FOR MAKING PEROXYCARBOXYLIC ACIDS

TECHNICAL FIELD

This invention relates to a safe method for making crystalline peroxides of carboxylic acids from the corresponding carboxylic acid and hydrogen peroxide in a concentrated acid reaction medium.

BACKGROUND ART

The following documents disclose continuous processes for producing peroxyacids or the like from hydrogen peroxide, sulfuric acid, and a carboxylic acid: U.S. Pat. No. 2,816,147, issued to Weber et al on Dec. 10, 1957; U.S. Pat. No. 3,140,312, issued to Kurhagec et al on July 7, 1964; U.S. Pat. No. 4,087,455, issued to Prescher et al on May 2, 1978; Canadian Pat. No. 744,391, issued to Wenzke, et al on Oct. 11, 1966; and U.S. Ser. No. 895,411, filed by Camden et al on Apr. 11, 1978 (the latter application is owned by the owners of the present application).

Numerous prior art references indicate the problem in the prior art of performing the present reaction safely, since if the reaction is not carefully controlled it can become uncontrollable, resulting in an exothermic reaction or even an explosion, or at least in an obstruction of the passages of the reaction apparatus. There is no recognition that use of a liquids:solvent ratio of greater than about 20:1 will provide that safety.

DISCLOSURE OF INVENTION

The inventors have discovered the use of a ratio of liquids to "solids" of greater than about 15:1 in a peroxidation process for carboxylic acids using a concentrated acid such as sulfuric acid as the reaction medium, provides a considerable improvement in safety. The process can be the continuous one disclosed in the copending application of Hutchins et al, U.S. Ser. No. 057,131, filed July 12, 1979 for "Continuous Process for Making Peroxy-Carboxylic Acids", said application being incorporated herein by reference. A preferred process, as disclosed hereinafter, utilizes particulate carboxylic acid and a preformed solution of hydrogen peroxide and the desired concentrated acid. These processes permit continuously and safely making a peroxyacid having about 6 to about 18, preferably about 8 to about 16 carbon atoms and at least one peroxyacid moiety, preferably such a compound with a peroxyacid moiety on each terminal carbon atom of an aliphatic straight-chain hydrocarbon moiety, and more preferably diperoxydodecanedioic acid.

In its broadest aspect the invention also includes batch processes and other chain lengths and carboxylic acids.

DETAILED DESCRIPTION OF THE INVENTION

The Process

The process of preparing peroxycarboxylic acids using a concentrated acid as the reaction mixture is also safer if the carboxylic acid is added to the preformed solution of concentrated acid and hydrogen peroxide in the form of small particles having a particle size of less than about 100 mesh, preferably about 200 mesh and dispersed therein with a high shear mixer. In a continuous process which recycles the acid and unreacted peroxide, additional concentrated acid and peroxide are added at the same time as the carboxylic acid to make up for losses, e.g., when the peroxy carboxylic acid is separated. The reaction mixture is then allowed to react for from about 15 to about 60, preferably from about 20 to about 40, minutes and the solid peroxycarboxylic acid particles are then separated from the liquid by filtration, centrifugation, etc. The product can then be purified, neutralized, etc. With this preferred process, a safer operation is possible down to a solids to liquid ratio of about 10:1, but for optimum safety the solids to liquid ratio should be above about 15:1. Since this process generates only a relatively small amount of heat, there is no need for a heat exchanger. Therefore, since conventional heat exchangers are enclosed, this process avoids creating an explosion hazard.

The concentrated acid concentration in the reaction mixture is from about 60% to about 80%, preferably from about 70% to about 77% and the hydrogen peroxide concentration is from about 2.5% to about 12.5%, preferably from about 2.5% to about 7.5%. The water level is from about 7.5% to about 27.5%, preferably from about 15.5% to about 24.5%.

The equilibrium reaction which forms the basis for the present process proceeds according to the following formula:

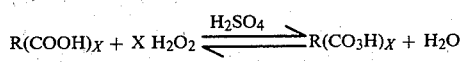

$$R(COOH)_x + X\, H_2O_2 \underset{}{\overset{H_2SO_4}{\rightleftarrows}} R(CO_3H)_x + H_2O$$

where R is an organic moiety and X is an integer. Since there is an equilibrium reaction, it was heretofore believed necessary to maintain a relatively concentrated reaction mixture and remove the product in order to drive the reaction toward completion. While it is still desired to remove some water to keep the process from becoming uneconomical, the process goes to completion readily with much more dilute mixtures than was previously thought to be acceptable. In the preferred continuous process this is accomplished without an organic solvent extraction step, and without requiring that the reaction mixture be distilled in order to separate the water of reaction and of dilution from the reaction products. The solid peroxyacid product which is separated entrains several (e.g., three) times its weight of the liquid components of the reaction mixture—of course, the exact amount entrained will depend on the mode of separation which is employed, the crystal size and distribution, and other factors. Using a centrifugal separation means as in the Example, the filtered solid product contains roughly 3 times its weight of entrained liquid. The reaction conditions can be adjusted so that the amounts of water, mineral acid, etc. in the entrained liquid reaction components are essentially equal to the amount of materials which are added to the recycled reaction mixture. Thus, provided that the process is run under such conditions that the material balance of incoming water and water of reaction is equal to the outgoing balance of entrained water, it is possible to maintain the proportion of water in the liquid portion of the reaction mixture at an essentially constant level.

The adjustment of the percentages of concentrated acid and hydrogen peroxide in the liquid portion of the reaction mixture is more straightforward. The concentrated acid is merely replaced as fast as it is removed from the reaction slurry as liquid entrained on the solid product, since the concentrated acid is neither created nor destroyed during the course of the present reaction. The amount of the carboxylic acid starting material which is added to the reaction mixture is adjusted to be just sufficient to replace the carboxylic acid starting material which is used up in the course of the reaction, plus the small amount, typically less than about 10%, of carboxylic acid starting material which remains in the reaction mixture after the time the product is separated. Likewise, the hydrogen peroxide which is consumed in the reaction or entrained in the filter cake is replaced in equal amount in the continuous process in order to maintain the concentration of hydrogen peroxide at the desired levels.

The Concentrated Acid

While in the preceding description of the invention, mineral (sulfuric) acid is the only reaction medium and catalyst described, those skilled in the art will find this invention to be readily adaptable to the use of other reaction media. Specific examples of alternate concentrated acids useful herein are phosphoric acid, pyrophosphoric acid, methane sulfonic acid, and phosphonic acid.

The Carboxylic Acid

The carboxylic acids which are preferred as starting materials in the present invention are organic acids having from about 6 to about 18, preferably about 8 to about 16 carbon atoms (especially from 11 to about 16 carbon atoms) and at least one carboxylic acid moiety. Preferred reactants are straight-chain aliphatic carboxylic acids having a carboxylic acid moiety on each of the terminal carbon atoms of the chain.

Specific examples of monocarboxylic acids which are useful in the practice of the present process are as follows: hexanoic (caproic) acid, heptanoic (enanthic) acid, octanoic (caprylic) acid, nonanoic (nonylic, pelargonic) acid, decanoic (capric, decylic) acid, undecanoic (hendecanoic, undecylic) acid, dodecanoic (lauric) acid, tridecanoic acid, tetradecanoic (myristic) acid, pentadecanoic (pentadecylic) acid, hexadecanoic (palmitic) acid, heptadecanoic (margaric) acid, octadecanoic (stearic) acid, nonadecanoic (nonadecylic) acid, and eicosanoic (arachic) acid. It will also be appreciated that mixtures of the above carboxylic acids are useful as starting materials in the present invention.

Examples of especially preferred carboxylic acid reactants of the present invention are the following dicarboxylic acids: 1,6-hexanedioic (adipic) acid, 1,7-heptanedioic (pimelic) acid, 1,8-octanedioic (suberic) acid, 1,9-nonanedioic (azelaic) acid, 1,10-decanedioic (sebacic) acid, 1,11-undecanedioic acid, 1,12-dodecanedioic acid, 1,13-tridecanedioic acid, 1,14-tetradecanedioic acid, 1,15-pentadecanedioic acid, 1,16-hexadecanedioic acid. 1,17-heptadecanedioic acid, 1,18-octadecanedioic acid, 1,19-nonadecanedioic acid, and 1,20-eicosanedioic acid. 1,12-dodecanedioic acid is the most preferred reactant. Other, similar peroxyacids may be used as reaction starting materials. Preferably their corresponding peroxyacid products are solids which are relatively insoluble in the reaction mixture. Again, mixtures of the above materials are within the scope of reactants which may be used to practice the present invention, as are mixtures of mono- and dicarboxylic acids.

The products which are formed as a result of the present process are peroxyacids corresponding to the carboxylic acid starting materials listed above. The product of the reaction may be a peroxyacid comprising a compound of 6 to 20 carbon atoms and at least one peroxyacid moiety, specifically, peroxyhexanoic acid, peroxyheptanoic acid, peroxyoctanoic acid peroxynonanoic acid, peroxydecanoic acid, peroxyundecanoic acid, peroxydodecanoic acid, peroxytridecanoic acid, peroxytetradecanoic acid, peroxypentadecanoic acid, peroxyhexadecanoic acid, peroxyheptadecanoic acid, peroxyoctadecanoic acid, peroxynonadecanoic acid, or peroxyeicosanoic acid.

Preferred products are straight-chain aliphatic compounds having 8 to 16 carbon atoms and a peroxyacid moiety on each terminal carbon atom. The preferred products produced according to the present process are 1,6-diperoxyhexanedioic acid, 1,7-diperoxyheptanedioic acid, 1,8-diperoxyoctanedioic acid, 1,9-diperoxynonanedioic acid, 1,10-diperoxydecanedioic acid, 1,11-diperoxyundecanedioic acid, 1,12-diperoxydodecanedioic acid, 1,13-diperoxytridecanedioic acid, 1,14-diperoxytetradecanedioic acid, 1,15-diperoxypentadecanedioic acid, 1,16-diperoxyhexadecanedioic acid, 1,17-diperoxyheptadecanedioic acid, 1,18-diperoxyoctadecanedioic acid, 1,19-diperoxynonadecanedioic acid, and 1,20-diperoxyeicosanedioic acid.

The diperoxyacids may be characterized by the following formula, where n may be 4 to 18 inclusive, preferably 6 to 14 inclusive (especially 9 to 14 inclusive):

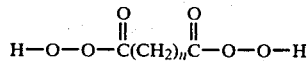

The most preferred reaction product is 1,12-diperoxydodecanedioic acid.

The indicated diperoxyacid products have utility as bleaching agents.

All parts, percentages and parts herein are by weight unless otherwise indicated.

EXAMPLE

The following is an example of operation of the present process in a continuous mode to produce peroxyacids under constant and safe conditions. This example is provided not to limit the scope of the invention but to illustrate a preferred mode of practice of the invention.

Dodecanedioic acid was ground to a #200 mesh particle size and fed to a high-shear mixer at the rate of about 94.4 pounds per hour along with 332 pounds per hour of a 75° F. aqueous solution containing 73.2% $H_2SO_4$ and 11.67%, $H_2O_2$, and the recycled liquid described hereinafter. The reaction mixture from the mixer at a temperature of 98° F. was routed through a 160 gallon plug flow reactor (100° F.) with a residence time of about 30 minutes. The aqueous reaction mixture contained, as a liquid, 76% $H_2SO_4$, 7% $H_2O_2$, and 20% $H_2O$ and, as a solid, 94% diperoxy dodecanedioic acid and 6% dodecanedioic acid for a liquid to solids ratio of about 40:1, the pounds of solids per hour being 106.6. The reaction mixture was run through a centrifugal separator and the product at a liquids to solids ratio of about 3:1 contained about 319.8 pounds per hour of liquid and about 106.6 pounds per hour of solids at a temperature of 100° F. The separated liquid was recycled to the high shear mixer.

The product was neutralized and spray dried to form particles of peroxy acid as described hereinafter.

Compositions Containing the Peroxyacid Compounds

The peroxyacid compounds made using the process of the present invention can be used in a wide variety of compositions. A preferred use, especially of diperoxydodecanedioic acid, is as a fabric bleaching agent. To insure that compositions containing the peroxyacid compounds are safe and effective, certain additives are desirably present.

It is well documented in the literature that peroxyacids are susceptible to a number of different stability problems, as well as being potentially hazardous compounds. Looking at the latter first, peroxyacids decompose exothermally and when the material is in dry granular form the heat generated must be controlled to make the product safe. The best exotherm control agents are those which are capable of liberating moisture at a temperature slightly below the decomposition temperature of the peroxyacid employed. U.S. Pat. No. 3,770,816, Nov. 6, 1973, to Nielsen, incorporated herein by reference, discloses a wide variety of hydrated materials which can serve as suitble exotherm control agents. Included among such materials are magnesium sulfate $.7H_2O$, magnesium formate dihydrate, calcium sulfate ($CaSO_4.2H_2O$), calcium lactate hydrate, calcium sodium sulfate ($CaSO_4.Na_2SO_4.2H_2O$), and hydrated forms of, for example, sodium aluminum sulfate, potassium aluminum sulfate, ammonium aluminum sulfate and aluminum sulfate. Preferred hydrates are the alkali metal aluminum sulfates; particularly preferred is potassium aluminum sulfate. Other preferred exotherm control agents are those materials which lose water as the result of chemical decomposition such as boric acid, malic acid and maleic acid. The exotherm control agent is preferably used in an amount of from about 100% to about 200% based on the weight of the peroxyacid compound.

The other problems faced when peroxyacid compounds are used fall into the area of maintaining good bleach effectiveness. It has been recognized that metal ions are capable of serving as catalyzing agents in the degradation of the peroxyacid compounds. To overcome this problem chelating agents can be used in an amount ranging from 0.005% to about 1.00% based on the weight of the composition to tie up heavy metal ions. U.S. Pat. No. 3,442,937, May 6, 1969, to Sennewald et al., discloses a chelating system comprising quinoline or a salt thereof, an alkali metal polyphosphate and, optionally, a synergistic amount of urea. U.S. Pat. No. 2,838,459, June 10, 1958, to Sprout, Jr., discloses a variety of polyphosphates as stabilizing agents for peroxide baths. These materials are useful herein as stabilizing aids. U.S. Pat. No. 3,192,255, June 29, 1965, to Cann, discloses the use of quinaldic acid to stabilize percarboxylic aids. This material, as well as picolinic acid and dipicolinic acid, would also be useful in the compositions of the present invention. A preferred chelating system for the present invention is a mixture of di picolinic acid and an acid polyphosphate, preferably acid sodium pyrophosphate. The latter can be a mixture of phosphoric acid and sodium pyrophosphate wherein the ratio of the former to the latter is from about 0.5:1 to about 2:1 and the ratio of the mixture to di picolinic acid is from about 1:8 to about 5:1.

In addition to the above-mentioned chelating systems to tie up heavy metals in the peroxyacid compositions, coating materials may also be used to extend the shelf life of dry granular compositions. Such coating materials may be, in general, acids, acid salts, esters, ethers and hydrocarbons and include such things as wide varieties of fatty acids, derivatives of fatty alcohols, such as esters and ethers, derivatives of polyethylene glycols, such as esters and ethers, and hydrocarbon oils and waxes. These materials aid in preventing moisture from reaching the peracid compound. Secondly, the coating material may be used to segregate the peracid compound from other agents which may be present in the composition and adversely affect the peracid's stability. When used in this manner the coating may be used on both the peracid compound and the other agent or either individually. The amount of the coating material used is generally from about 2.5% to about 15% based on the weight of the peroxyacid compounds.

Additional agents which may be used to aid bleaching performance include pH adjustment agents, bleach activators and minors such as coloring agents, dyes and perfumes. Typical pH adjustment agents are used to alter or maintain aqueous solutions of the instant compositions with the 5 to 10.5 pH range in which peroxyacid bleaching agents are generally most useful. Depending upon the nature of other optional composition ingredients, pH adjustment agents can be either acidic or basic. Acidic pH adjustment agents (designed to compensate for the presence of other highly alkaline materials) include normally solid organic and inorganic acids, acid mixtures and acid salts. Examples of such acidic pH adjustment agents include citric acid, glycolic acid, tartaric acid, gluconic acid, glutamic acid, sulfamic acid, sodium bisulfate, potassium bisulfate, ammonium bisulfate and mixtures of citric acid and lauric acid. Citric acid is preferred by virtue of its low toxicity and hardness sequestering capability.

Optional alkaline pH adjustment agents include the conventional alkaline buffering agents. Such buffering agents include such salts as carbonates, bicarbonates, silicates, pyrophosphates and mixtures thereof. Sodium bicarbonate and tetrasodium pyrophosphate are highly preferred.

Optional peroxyacid bleach activators suggested by the prior art include such materials as aldehydes and ketones. Use of these materials as bleaching activators is described more fully in U.S. Pat. No. 3,822,114, issued July 2, 1974 to Montgomery, incorporated herein by reference.

Optional ingredients, if utilized in combination with the active peroxyacid of the instant invention to form a complete bleaching product, may comprise from about 20% to about 99% by weight of the total composition. Conversely, the peroxyacid compound made using the process of the present invention may comprise from about 1% to about 80% of the composition.

The bleaching compositions of the instant invention, particularly the dry granular version, can also be added to and made a part of conventional fabric laundering detergent compositions. Accordingly, optional materials for the instant bleaching compositions can include such standard detergent adjuvants as surfactants and builders. Optional surfactants are selected from the group consisting of organic anionic, nonionic, ampholytic, and zwitterionic surfactants and mixtures thereof. Optional builder materials include any of the conventional organic and inorganic builder salts including carbonates, silicates, acetates, polycarboxylates and phosphates. If the instant stabilized bleaching compositions are employed as part of a conventional fabric laundering detergent composition, the instant bleaching agent generally comprises from about 1% to about 40% by weight of such conventional detergent compositions. Conversely, the instant bleaching compositions can optionally contain from about 60% to about 99% by weight of conventional surfactant and builder materials. Further examples of suitable surfactants and builders are given below.

Water-soluble salts of the higher fatty acids, i.e., "soaps," are useful as the anionic surfactant herein. This class of surfactants includes ordinary alkali metal soaps such as the sodium, potassium, ammonium and alkanolammonium salts of the higher fatty acids containing from about 8 to about 24 carbon atoms and preferably from about 10 to about 20 carbon atoms. Soaps can be made by direct saponification of fats and oils by the neutralization of free fatty acids. Particularly useful are the sodium and potassium salts of the mixtures of fatty acids derived from coconut oil and tallow, i.e., sodium or potassium tallow or coconut soaps.

Another class of anionic surfactants includes water-soluble salts, particularly the alkali metal, ammonium and alkanolammonium salts, of organic sulfuric reaction products having in their molecular structure an alkyl group containing from about 8 to about 22 carbon atoms and a sulfonic acid or sulfuric acid ester group. (Included in the term "alkyl" is the alkyl portion of acyl groups.) Examples of this group of synthetic surfactants which can be used in the present detergent compositions are the sodium and potassium alkyl sulfates, especially those obtained by sulfating the higher alcohols produced by reducing the glycerides of tallow or coconut oil; and sodium and potassium alkyl benzene sulfonates, in which the alkyl group contains from about 9 to about 15 carbon atoms in straight chain or branched chain configuration, e.g., those of the type described in U.S. Pat. Nos. 2,220,099, and 2,477,383, incorporated herein by reference.

Other anionic surfactant compounds useful herein include the sodium alkyl glyceryl ether sulfonates, especially those ethers or higher alcohols derived from tallow and coconut oil; sodium coconut oil fatty acid monoglyceride sulfonates and sulfates; and sodium or potassium salts of alkyl phenol ethylene oxide ether sulfates containing about 1 to about 10 units of ethylene oxide per molecule and wherein the alkyl groups contain about 8 to about 12 carbon atoms.

Other anionic surfactants useful herein include the water-soluble salts of esters of alpha-sulfonated fatty acids containing from about 6 to 20 carbon atoms in the ester group; water-soluble salts of 2-acyloxy-alkanel-sulfonic acids containing from about 2 to about 9 carbon atoms in the acyl group and from about 9 to 23 carbon atoms in the alkane moiety; alkyl ether sulfates containing from about 10 to 24 carbon atoms in the alkyl group and from about 1 to 30 moles of ethylene oxide; water-soluble salts of olefin sulfonates containing from about 12 to 24 carbon atoms; and β-alkyloxy alkane sulfonates containing from about 1 to 3 carbon atoms in the alkyl group and from about 8 to 20 carbon atoms in the alkane moiety.

Preferred water-soluble anionic organic surfactants herein include linear alkyl benzene sulfonates containing from about 11 to 14 carbon atoms in the alkyl group; the tallow alkyl sulfates; the coconut alkyl glyceryl sulfonates; and alkyl ether sulfates wherein the alkyl moiety contains from about 14 to 18 carbon atoms and wherein the average degree of ethoxylation varies between 1 and 6.

Specific preferred anionic surfactants for use herein include: sodium linear $C_{10}$–$C_{12}$ alkyl benzene sulfonate; triethanolamine $C_{10}$–$C_{12}$ alkyl benzene sulfonate; sodium tallow alkyl sulfate; sodium coconut alkyl glyceryl ether sulfonate; and the sodium salt of a sulfated condensation product of tallow alcohol with from about 3 to about 10 moles of ethylene oxide.

It is to be recognized that any of the foregoing anionic surfactants can be used separately herein or as mixtures.

Nonionic surfactants include the water-soluble ethoxylates of $C_{10}$–$C_{20}$ aliphatic alcohols and $C_6$–$C_{12}$ alkyl phenols. Many nonionic surfactants are especially suitable for use as suds controlling agents in combination with anionic surfactants of the type disclosed herein.

Semi-polar surfactants useful herein include water-soluble amine oxides containing one alkyl moiety of from about 10 to 28 carbon atoms and 2 moieties selected from the group consisting of alkyl groups and hydroxyalkyl groups containing from 1 to about 3 carbon atoms; water-soluble phosphine oxides containing one alkyl moiety of about 10 to 28 carbon atoms and 2 moieties selected from the group consisting of alkyl groups and hydroxyalkyl groups containing from about 1 to 3 carbon atoms; and water-soluble sulfoxides containing one alkyl moiety of from about 10 to 28 carbon atoms and a moiety selected from the group consisting of alkyl and hydroxyalkyl moieties of from 1 to 3 carbon atoms.

Ampholytic surfactants include aliphatic derivatives of heterocyclic secondary and tertiary amines in which the aliphatic moiety can be a branched or straight chain and wherein one of the aliphatic substituents contains from about 8 to 18 carbon atoms and at least one aliphatic substituent contains an anionic water-solubilizing group.

Zwitterionic surfactants include derivatives of aliphatic quaternary ammonium, phosphonium and sulfonium compounds in which the aliphatic moieties can be straight or branched chains, and wherein one of the aliphatic substituents contains from about 8 to 18 carbon atoms and one of the aliphatic substituents contains an anionic water-solubilizing group.

The instant granular compositions can also comprise those detergency builders commonly taught for use in laundry compositions. Useful builders herein include any of the conventional inorganic and organic water-soluble builder salts, as well as various water-insoluble builders and so-called "seeded" builders.

Inorganic detergency builders useful herein include, for example, water-soluble salts of phosphates, pyrophosphates, orthophosphates, polyphosphates, phosphonates, carbonates, bicarbonates, borates and silicates. Specific examples of inorganic phosphate builders include sodium and potassium tripolyphosphates, phosphates, and hexametaphosphates. The polyphosphates also specifically include, for example, the sodium and potassium salts of ethylene diphosphonic acid, the sodium and potassium salts of ethane 1-hydroxy-1, 1-diphosphonic acid, and the sodium and potassium salts of ethane-1,1,2-triphosphonic acid. Examples of these and other phosphorus builder compounds are disclosed in U.S. Pat. Nos. 3,159,581; 3,213,030; 3,422,021; 3,422,137; 3,400,176 and 3,400,148, incorporated herein by reference. Sodium tripolyphosphate is an especially preferred, water-soluble inorganic builder herein.

Nonphosphorus containing sequestrants can also be selected for use herein as detergency builders. Specific examples of nonphosphorus, inorganic builder ingredients include water-soluble inorganic carbonate, bicarbonate, borate and silicate salts. The alkali metal, e.g., sodium and potassium carbonates, bicarbonates, borates (including borax) and silicates are particularly useful herein.

Water-soluble, organic builders are also useful herein. For example, the alkali metal, ammonium and substituted ammonium polyacetates, carboxylates, polycarboxylates, succinates, and polyhydroxysulfonates are useful builders in the present compositions and processes. Specific examples of the polyacetate and polycarboxylate builder salts include sodium, potassium, lithium, ammonium and substituted ammonium salts of ethylene diamine tetraacetic acid, nitrilotriacetic acid, oxydisuccinic acid, melittic acid, benzene polycarboxylic acids, and citric acid.

Highly preferred nonphosphorous builder materials (both organic and inorganic) useful herein include sodium carbonate, sodium bicarbonate, sodium silicate, sodium citrate, sodium oxydisuccinate, sodium mellitate, sodium nitrilotriacetate, and sodium ethylene diamine tetraacetate, and mixtures thereof.

Another type of detergency builder material useful in the present compositions and processes comprises a water-soluble material capable of forming a water-insoluble reaction product with water hardness cations in combination with a crystallization seed which is capable of providing growth sites for said reaction product.

Specific examples of materials capable of forming such water-insoluble reaction products include the water-soluble salts of carbonates, bicarbonates, sesquicarbonates, silicates, aluminates and oxalates. The alkali metal, especially sodium, salts of the foregoing materials are preferred for convenience and economy.

Another type of builder useful herein includes various substantially water-insoluble materials which are capable of reducing the hardness content of laundering liquors, e.g., by ion-exchange processes. Examples of such builder materials include the phosphorylated cloths disclosed in U.S. Pat. No. 3,424,535, Bauman, issued Jan. 28, 1969, incorporated herein by reference.

The complex aluminosilictes, i.e., zeolite-type materials, are useful presoaking/washing adjuvants herein in that these materials soften water, i.e., remove $Ca^{++}$ hardness. Both the naturally occurring and synthetic "zeolites," especially zeolite A and hydrated zeolite A materials, are useful for this builder/softener purpose. A description of zeolite builder materials appears in Krummel et al, U.S. Pat. No. 3,985,669, issued Oct. 12, 1976, incorporated herein by reference.

A preferred dry, granular bleaching product employing the peroxyacid bleach of the present invention is made by combining the active peroxy compound with potassium aluminum sulfate or boric acid, the acid pyrophosphate/dipicolinic acid chelating system, sodium sulfate, and linear alkyl benzene sulfonate, and subsequently coating this mixture with mineral oil.

Composition Preparation

The bleaching compositions of the instant invention are prepared in any conventional manner such as by admixing ingredients, by agglomeration, by compaction, by granulation, or by spray drying or prilling and fluid bed drying in the case of the dry granular form. A preferred method for forming the granular product is fluid bed drying. The diperoxyacid and other components of the granule are thoroughly mixed in an agitated tank with sufficient water to form a smooth paste. This paste is atomized into the top of a conventional spray drying tower (either countercurrent air flow or cocurrent air flow) using a high pressure pump (500–1000 pounds per inch absolute, or $3.5 \times 10^5$ to $7.0 \times 10^5$ $kg/m^2$) and a nozzle setup. The atomized particles fall through the air stream which has been preheated to about 400° F. (200° C.) and are collected at the base of the tower. Inlet air conditions and product flow rate are adjusted to give an outlet air temperature of about 100°–150° F. (38°–66° C.) and a product moisture content of about 5% to 10%. One skilled in the art will recognize that these conditions are similar to those employed in spray drying any heat sensitive material such as powdered milk or the like. The spray dried granules are further dried in a mild, low temperature manner such as a fluid bed dryer with an inlet air temperature of 120°–140° F. (49°–60° C.). This two-stage drying operation yields a very dry granule which typically improves stability and minimizes activity losses during the drying operation.

Bleaching granules prepared in this manner can then be admixed with other granules of optional bleaching detergent composition materials. The particle size of the bleach-containing granules is important since smaller sizes, e.g., less than about 100 mesh are not sufficiently stable. The particle size of optional granules of additional material is not critical except to avoid segregation. If, however, compositions are to be realized having commercially acceptable flow properties, certain granule size limitations are highly preferred. In general, all granules of the instant compositions preferably range in size from about 100 microns to 3000 microns, more preferably from about 100 microns to 1300 microns.

Additionally, flowability is enhanced if particles of the present invention are of approximately the same size. Therefore, preferably the ratio of the average particle sizes of the bleach-containing granules and optional granules of other materials has a value between 0.5:1 and 2.0:1.

Bleaching compositions of the present invention are utilized by dissolving them in water in an amount sufficient to provide from about 1.0 ppm to 100 ppm available oxygen in solution. Generally, this amounts to about 0.005% to 0.5% by weight of composition in solution. Fabrics to be bleached are then contacted with such aqueous bleaching solutions.

What is claimed is:

1. An improved process for making a peroxyacid having about 6 to about 18 carbon atoms and at least one peroxyacid moiety, comprising the step of:
   (a) preparing a reaction slurry comprising a liquid phase and a solid phase;
      i. said liquid phase comprising 60 to 80% by weight of the mixture of concentrated acid selected from the group consisting of sulfuric acid, methane sulfuric acid, phosphonic acid, phosphoric acid, pyrophosphonic acid, and mixtures thereof; 2.5 to 12.5% by weight of the mixture of hydrogen peroxide; and 7.5 to 37.5% by weight of the mixture of water, and
      ii. said solid phase comprising a peroxyacid having about 6 to about 18 carbon atoms and the carboxylic acid starting material corresponding to said peroxyacid;

in a reaction vessel at a temperature between about 15 degrees Celsius and 50 degrees Celsius; the ratio of the liquid phase to the solid phase being from about 15:1 to about 49:1.

2. An improved process for making a peroxyacid having about 6 to about 18 carbon atoms and at least one peroxyacid moiety, comprising the step of:

(a) preparing a reaction slurry comprising a liquid phase and a solid phase;
  i. said liquid phase comprising 60 to 80% by weight of the mixture of concentrated acid selected from the group consisting of sulfuric acid, methane sulfuric acid, phosphonic acid, phosphoric acid, pyrophosphonic acid, and mixtures thereof; 2.5 to 12.5% by weight of the mixture of hydrogen peroxide; and 7.5 to 37.5% by weight of the mixture of water, and
  ii. said solid phase comprising a peroxyacid having about 6 to about 18 carbon atoms and the carboxylic acid starting material corresponding to said peroxyacid;

in a reaction vessel at a temperature between about 15 degrees Celsius and 50 degrees Celsius; the ratio of the liquid phase to the solid phase being from about 10:1 to about 49:1, said carboxylic acid starting material being added to the preformed mixture of concentrated acid and hydrogen peroxide in the form of particles having a size of less than about 100 mesh.

3. The invention of claims 1 or 2 wherein said peroxyacid has from about 8 to about 16 carbon atoms.

4. The process of claim 1 wherein the weight ratio of said liquid phase with respect to said solid phase is at least about 30:1.

5. The process of claim 4 wherein the weight ratio of said liquid phase with respect to said solid phase is at least about 40:1.

6. The process of claims 1 or 2 wherein said liquid phase comprises 70 to 77% by weight of the mixture of sulfuric acid, 2.5 to 7.5% by weight of the mixture of hydrogen peroxide, and 15.5 to 27.5% by weight of the mixture of water.

7. The process of claim 6 wherein said liquid phase comprises 71 to 75% by weight of the mixture of sulfuric acid, 4.5% to 7.5% by weight of the mixture of hydrogen peroxide, and 17.5% to 24.5% by weight of the mixture of water.

* * * * *